United States Patent
Weiner et al.

(10) Patent No.: US 9,266,095 B2
(45) Date of Patent: Feb. 23, 2016

(54) HYDROGENATION CATALYSTS WITH COBALT AND ALKALINE-EARTH METAL MODIFIED SUPPORTS

(71) Applicant: Celanese International Corporation, Irving, TX (US)

(72) Inventors: Heiko Weiner, Pasadena, TX (US); Zhenhua Zhou, Houston, TX (US); Dick Nagaki, The Woodlands, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 38 days.

(21) Appl. No.: 14/164,656

(22) Filed: Jan. 27, 2014

(65) Prior Publication Data
US 2015/0209762 A1    Jul. 30, 2015

(51) Int. Cl.
| | |
|---|---|
| B01J 23/40 | (2006.01) |
| B01J 23/58 | (2006.01) |
| B01J 23/78 | (2006.01) |
| B01J 23/75 | (2006.01) |
| B01J 23/62 | (2006.01) |
| B01J 23/648 | (2006.01) |
| C07C 1/24 | (2006.01) |
| C07C 29/149 | (2006.01) |
| B01J 37/02 | (2006.01) |
| B01J 23/42 | (2006.01) |
| B01J 23/44 | (2006.01) |
| B01J 23/89 | (2006.01) |
| B01J 35/02 | (2006.01) |

(52) U.S. Cl.
CPC *B01J 23/75* (2013.01); *B01J 23/42* (2013.01); *B01J 23/44* (2013.01); *B01J 23/626* (2013.01); *B01J 23/6482* (2013.01); *B01J 23/892* (2013.01); *B01J 23/8926* (2013.01); *B01J 23/8966* (2013.01); *B01J 35/026* (2013.01); *B01J 37/0201* (2013.01); *B01J 37/0207* (2013.01); *B01J 37/0244* (2013.01); *C07C 1/24* (2013.01); *C07C 29/149* (2013.01); *B01J 2523/00* (2013.01)

(58) Field of Classification Search
CPC ............ B01J 21/12; B01J 23/40; B01J 23/58; B01J 23/78
USPC ............................ 568/903; 502/185, 560, 326
See application file for complete search history.

(56) References Cited

U.S. PATENT DOCUMENTS

| | | | |
|---|---|---|---|
| 4,398,039 A | 8/1983 | Pesa et al. | |
| 4,517,391 A | 5/1985 | Schuster et al. | |
| 4,777,303 A | 10/1988 | Kitson et al. | |
| 4,804,791 A | 2/1989 | Kitson et al. | |
| 4,835,131 A | 5/1989 | DeJong | |
| 5,149,680 A | 9/1992 | Kitson et al. | |
| RE35,377 E | 11/1996 | Steinberg et al. | |
| 5,821,111 A | 10/1998 | Grady et al. | |
| 6,204,417 B1 | 3/2001 | Fischer et al. | |
| 6,232,352 B1 | 5/2001 | Vidalin | |
| 6,495,730 B1 | 12/2002 | Konishi et al. | |
| 6,657,078 B2 | 12/2003 | Scates et al. | |
| 6,685,754 B2 | 2/2004 | Kindig et al. | |
| 7,375,049 B2 | 5/2008 | Hayes et al. | |
| 7,608,744 B1 | 10/2009 | Johnston et al. | |
| 7,863,489 B2 | 1/2011 | Johnston et al. | |
| 8,211,821 B2 | 7/2012 | Weiner et al. | |
| 8,211,823 B2 | 7/2012 | Liang et al. | |
| 8,309,772 B2 | 11/2012 | Weiner et al. | |
| 8,471,075 B2 | 6/2013 | Johnston et al. | |
| 8,501,652 B2 * | 8/2013 | Johnston et al. | 502/100 |
| 8,536,382 B2 | 9/2013 | Jevtic et al. | |
| 8,865,609 B2 | 10/2014 | Zhou et al. | |
| 2010/0030001 A1 | 2/2010 | Chen et al. | |
| 2010/0030002 A1 | 2/2010 | Johnston et al. | |
| 2012/0165589 A1 | 6/2012 | Partington | |
| 2012/0296111 A1 | 11/2012 | Konigsmann et al. | |
| 2013/0178661 A1 | 7/2013 | Zhou et al. | |
| 2013/0178663 A1 | 7/2013 | Zhou et al. | |

FOREIGN PATENT DOCUMENTS

| | | |
|---|---|---|
| CN | 103113187 A | 5/2013 |
| EP | 0175558 | 3/1986 |
| EP | 2 583 751 A1 | 4/2013 |
| WO | 2010/146332 A1 | 12/2010 |
| WO | 2011/094713 A1 | 8/2011 |
| WO | 2013/101756 A1 | 7/2013 |
| WO | 2013/103850 A1 | 7/2013 |

OTHER PUBLICATIONS

International Search Report and Written Opinion of the International Searching Authority mailed on Jun. 16, 2015 for PCT Patent Application No. PCT/US2015/013122, 12 pages.

* cited by examiner

*Primary Examiner* — Mark Shibuya
*Assistant Examiner* — Janet L Coppins
(74) *Attorney, Agent, or Firm* — Kilpatrick Townsend & Stockton LLP

(57) ABSTRACT

A process for selective formation of ethanol from acetic acid by hydrogenating acetic acid in the presence of a catalyst comprising a modified support having cobalt and an alkaline earth support modifier. The active metals may include a first metal of palladium, platinum, and combinations thereof and a second metal of copper, iron, nickel, zinc, silver, chromium, tin, and combinations thereof.

18 Claims, No Drawings

HYDROGENATION CATALYSTS WITH COBALT AND ALKALINE-EARTH METAL MODIFIED SUPPORTS

FIELD OF THE INVENTION

The present invention relates generally to processes for hydrogenating acetic acid to form ethanol and to novel catalysts for use in such processes and their preparation, the catalysts having modified supports comprising cobalt and alkaline-earth metals.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

As an alternative to fermentation, ethanol may be produced by hydrogenating acetic acid and esters thereof. Ethanol production via the reduction of acetic acid generally uses a hydrogenation catalyst. The reduction of various carboxylic acids over metal oxides has been proposed by EP0175558 and U.S. Pat. No. 4,398,039. U.S. Pat. No. 7,608,744 describes a process for the selective production of ethanol by vapor phase reaction of acetic acid at a temperature of about 250° C. over a hydrogenating catalyst composition either cobalt and palladium supported on graphite or cobalt and platinum supported on silica. U.S. Pat. No. 7,863,489 describes a process for the selective production of ethanol by vapor phase reaction of acetic acid over a hydrogenation catalyst composition to form ethanol is disclosed and claimed. In an embodiment of this invention, reaction of acetic acid and hydrogen over a platinum and tin supported on silica, graphite, calcium silicate or silica-alumina in a vapor phase at a temperature of about 250° C. U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising platinum and rhenium. U.S. Pat. No. 5,149,680 describes catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another production process of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process wherein a predominantly cobalt-containing catalyst is used and acetic acid and hydrogen are passed through the reactor, at from 210 to 330° C., and under 10 to 350 bar, under conditions such that a liquid phase is not formed during the process.

Previous hydrogenation catalysts suffered from several drawbacks that did not favor industrial production of ethanol. These drawbacks included low catalyst lifetime, productivity, and co-production of byproducts. One solution for improving productivity and reducing co-production of byproducts, and in particular ethyl acetate, was to enhance the support with a basic modifier. This also increased selectivity to ethanol. Hydrogenation catalysts having supports with basic modifiers have previously been disclosed. U.S. Pat. No. 8,309,772 discloses a process for selective formation of ethanol from acetic acid and includes contacting a feed stream containing acetic acid and hydrogen at an elevated temperature with catalyst comprising platinum and tin on a high surface area silica promoted with calcium metasilicate. U.S. Pat. No. 8,471,075 also discloses a process for selective formation of ethanol from acetic acid by hydrogenating acetic acid in the presence of first metal, a silicaceous support, and at least one support modifier. The support modifier, e.g., metasilicate support modifier, may be selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group JIB metal metasilicates, (vii) Group IIIB metal oxides, (viii) Group IIIB metal metasilicates, and mixtures thereof.

One disadvantage is supports having basic modifiers tend to show a low conversion of acetic acid. Low conversion generally requires a larger acetic acid recycle. Higher amounts of precious metals may be needed to compensate for low conversions. In addition, the hydrogenation catalysts with supports having basic modifiers are not suitable for converting ethyl acetate. Thus, ethyl acetate needs to be removed from the recycle stream to avoid the buildup stream of ethyl acetate in the reactor.

Thus, further improvements to hydrogenation catalysts having supports with basic modifiers to increase conversion of acetic acid are needed to improve production of ethanol from acetic acid.

SUMMARY OF THE INVENTION

In accordance with the invention, we have surprisingly found that the problems discussed above can be remedied through the use of a catalyst for hydrogenating acetic acid and esters thereof, comprising: a first active metal selected from the group consisting of palladium, platinum, and combinations thereof, and a second active metal selected from the group consisting of copper, iron, nickel, zinc, silver, chromium, tin, and combinations thereof; and a modified support, wherein the active metals are disposed on the modified supports, wherein the modified support further comprises a support material selected from the group consisting of silica, silica/alumina, pyrogenic silica, high purity silica, carbon, and mixtures thereof, and support modifiers comprising from 0.2 wt. % to 10 wt. %, preferably from 3 wt. % to 9 wt. %, of a first modifier selected from the group consisting of oxides of cobalt, and from 0.2 wt. % to 25 wt. %, preferably from 3 wt.

% to 9 wt. %, of a second modifier selected from the group consisting of alkaline earth metal oxides or metasilicates of the alkaline earth metals, where the first metal is present in an amount of less than 1 wt. %, preferably from 0.3 to 0.7 wt. %, and the total content of the first and second metals is in an amount from 0.1 wt. % to 10 wt. %, based on the total weight of the catalyst. In certain embodiments, the second metal can be tin and/or the second modifier can be calcium metasilicate. In one aspect, the oxides of cobalt may comprise a mixture of cobalt and vanadium oxide.

In some embodiments, the catalyst and/or the modified support is substantially free of ruthenium, rhenium, tungsten, molybdenum, niobium, and tantalum. In addition, the catalyst and/or the modified support is substantially free of alkali metals.

For purposes of the present invention, cobalt is present as a support modifier and not an active metal. As stated above the active metals may include palladium, platinum, copper, iron, nickel, zinc, silver, chromium, tin, and combinations thereof, provided that the active metals are substantially free of cobalt and oxides thereof.

In other embodiments, the invention can relate to a catalyst for hydrogenating acetic acid, comprising platinum, metal oxides of tin and cobalt, and an oxide or metasilicate of an alkaline earth metal, dispersed on a silicaceous support.

In another embodiment, the invention can relate to a process for producing ethanol, comprising contacting a feed stream comprising acetic acid, ethyl acetate, or mixtures thereof and hydrogen in a reactor in the presence of a catalyst comprising platinum, metal oxides of tin and cobalt, an oxide or metasilicate of an alkaline earth metal, and a silicaceous support, under conditions effective to form ethanol. In one aspect, the feed stream further comprises ethyl acetate in an amount greater than 5 wt. %. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof. The process may further comprise dehydrating the ethanol obtained during the hydrogenation to produce ethylene.

The hydrogenation catalysts of the present invention may have a selectivity to ethanol of at least 80% and is not selective to methane, ethane, carbon dioxide, diethyl acetate, diethyl ether.

In another embodiment, the invention can relate to a process for producing ethanol, comprising contacting acetic acid and/or ethyl acetate and hydrogen in a reactor in the presence of a catalyst under conditions effective to form ethanol, wherein the catalyst comprises active metals comprising: a first metal selected from the group consisting of palladium, platinum, and combinations thereof, and a second metal selected from the group consisting of copper, iron, nickel, zinc, silver, chromium, tin, and combinations thereof; and b) a modified support, wherein the active metals are disposed on the modified supports, wherein the modified support further comprises: 1) a support material selected from the group consisting of silica, silica/alumina, pyrogenic silica, high purity silica, carbon, and mixtures thereof, and 2) support modifiers comprising: i) from 0.2 wt. % to 10 wt. % of a first modifier selected from the group consisting of oxides of cobalt, and ii) from 0.2 wt. % to 25 wt. % of a second modifier selected from the group consisting of alkaline earth metal oxides or metasilicates of the alkaline earth metals, wherein the first metal is present in an amount of less than 1 wt. % and the total content of the first and second metals is in an amount from 0.1 wt. % to 10 wt. %, based on the total weight of the catalyst.

In yet another embodiment, the invention can relate to a process for making a catalyst involving impregnating a support material with a cobalt precursor and support modifier precursor to form a first impregnated support, wherein the support modifier precursor comprises an alkaline earth metal; heating the first impregnated support to a first temperature to form a modified support; impregnating the modified support with a metal precursor solution to form a second impregnated support, wherein the metal precursor solution comprises a first metal precursor to a first metal selected from the group consisting of palladium and platinum and a second metal precursor to a second metal selected from the group consisting of copper, iron, nickel, zinc, silver, chromium, and tin; and heating the second impregnated support to a second temperature to form the catalyst.

In yet another embodiment, the invention can relate to a process for making a catalyst involving impregnating a support material comprising silica and calcium with a cobalt precursor to form a first impregnated support; heating the first impregnated support to a first temperature to form a modified support; impregnating the modified support with a metal precursor solution to form a second impregnated support, wherein the metal precursor solution comprises a first metal precursor to a first metal selected from the group consisting of palladium and platinum and a second metal precursor to a second metal selected from the group consisting of copper, iron, nickel, zinc, silver, chromium, and tin; and heating the second impregnated support to a second temperature to form the catalyst.

DETAILED DESCRIPTION OF THE INVENTION

The present invention relates to processes for producing ethanol by hydrogenating acetic acid and/or ethyl acetate in the presence of a catalyst with cobalt and alkaline earth metal-modified supports. The invention also relates to catalysts and methods for preparing the catalysts. The hydrogenation reaction of a carboxylic acid, acetic acid in this example, may be represented as follows:

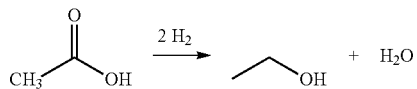

It has surprisingly and unexpectedly been discovered that the catalysts of the present invention provide high conversion of acetic acid and high selectivities to ethoxylates, such as ethanol and ethyl acetate, and in particular to ethanol, when employed in the hydrogenation of carboxylic acids such as acetic acid. Embodiments of the present invention beneficially may be used in industrial applications to produce ethanol on an economically feasible scale.

The catalysts generally comprise active metals on a modified support. In one embodiment, the modified support comprises (i) a support material; (ii) a first support modifier selected from the group comprising the oxides of cobalt; and (iii) a second support modifier selected from the group consisting of alkaline earth metal oxides or metasilicates of the alkaline earth metals. Preferably, the active metals may include a first metal and a second metal. In one embodiment, the first metal is selected from the group consisting of palladium, platinum, or combinations thereof, and the second metal is selected from the group consisting of copper, iron, nickel, zinc, silver, chromium, tin, and combinations thereof. In some embodiments the first metal can be present in low amounts of less than 1 wt. % based on the total weight of the catalyst. Advantageously, the modified supports of the present invention may reduce the loadings of the first metals translating into reduced catalyst costs. Also, in some embodiments, the total content of first and second metals may be in an amount from 0.1 to 10 wt. % based on the total weight of the catalyst. Regarding the modified support, it may comprise from 0.2 to 10 wt. % of cobalt oxides, e.g., from 0.2 to 5 wt. %., from 0.5 to 4 wt. %, from 1 to 4 wt. %, from 3 to 4 wt. % cobalt oxides, etc., and another support modifier, preferably a basic support modifier, in an amount from 0.2 to 25 wt. %, e.g. from 0.2 to 5 wt. %., from 0.5 to 4 wt. %, from 1 to 4 wt. %, from 3 to 4 wt. %, etc., based on the total weight of the modified support. In some aspects, the oxides of cobalt may comprise oxides of cobalt and vanadium. Ratios of cobalt oxide to the other support modifier, i.e. alkaline earth metal, can vary from, for example, 20:1 to 1:10, e.g., from 5:1 to 1:5, from 5:1 to 1:1, etc. Preferably, the modified support does not comprise the first and second active metals. Similarly, preferably the active metals are substantially free of cobalt and/or cobalt oxides. In other words, cobalt in the catalyst is present as a support modifier and not as an active metal. In this function, without being bound by theory, cobalt when used in relatively low loadings as a support modifier may stabilize the active metals to increase the selectivity of the reaction, and increase catalyst stability and lifetime. Advantageously, lower loadings of active metals, in particular, platinum and palladium, may be used leading to lower catalyst costs. In addition, it is preferred that the catalyst and modified support are substantially free of ruthenium, rhenium, tungsten, molybdenum, niobium, and tantalum.

Active Metals

The catalyst of the invention comprises at least two active metals, e.g., a first metal and a second metal. In some embodiments, the catalyst may comprise additional active metals. In this context, the numerical terms "first," "second," "third," etc., when used to modify the word "metal," are meant to indicate that the respective metals are different from one another. The total weight of all supported metals present in the catalyst preferably is from 0.1 to 10 wt. %, e.g., from 0.1 to 8 wt. %, or from 0.5 wt. % to 7.5 wt. %. For purposes of the present specification, unless otherwise indicated, weight percent is based on the total weight of the catalyst including metal and support. The metal(s) in the catalyst may be present in different forms, for example in the form of one or more metal oxides. For purposes of determining the weight percent of the metal(s) in the catalyst, the weight of any oxygen that is bound to the metal is ignored.

Since the catalyst includes two or more metals, one metal may act as the main active metal while another metals acts as a promoter metal. For instance, with a platinum/tin catalyst, platinum may be considered to be the main metal and tin may be considered the promoter metal. For convenience, the present specification refers to the first metal as the primary catalyst and the second metal (and other optional metals) as the promoter(s). This should not be taken as an indication of the underlying mechanism of the catalytic activity. In some embodiments, the two or more active metals may be alloyed with one another or may comprise a non-alloyed metal solution or mixture.

As stated above, the first metal may be palladium, platinum, or combinations thereof. Preferably, the first metal does not comprise ruthenium. The loading of the first metal is preferably less than the loading of the second metal. Lower loadings of the first metal are preferred to reduce costs. In one embodiment, the first metal may be present in an amount from 0.05 to 5 wt. %, e.g. from 0.1 to 3 wt. %, from 0.1 to 1.2 wt. %, or from 0.3 to 0.7 wt. %.

As indicated above, the catalyst further comprises a second metal, which typically would function as a promoter. The second metal preferably is selected from the group consisting of copper, iron, nickel, zinc, silver, chromium, tin, and combinations thereof. More preferably, the second metal is selected from the group consisting of copper, iron, nickel, and tin. More preferably, the second metal comprises tin. Preferably, the second metal does not comprise rhenium, tungsten, molybdenum, niobium, and tantalum. The second metal loading preferably is from 0.1 and 10 wt. %, e.g., from 0.5 to 8 wt. %, or from 1 to 5 wt. %. Similar to the first metal, it is preferable to reduce the loading of the second metal and loadings of less than 5 wt. % are preferred. When additional active metals are used, the additional metals may be selected from the first or second active metals. The loadings of these additive active metals may be from 0.05 and 4 wt. %, e.g., from 0.1 to 3 wt. %, or from 0.1 to 2 wt. %. The total content of the first and second active metals is less than the amount of the first modifier.

The active metals are substantially free of cobalt and oxides thereof. Although cobalt is added to the support material to form the modified support, no cobalt is added to the modified support as an active metal. In this regard, without being bound by theory, cobalt functions to stabilize the active metal(s).

Exemplary active metal combinations for the catalyst of the present invention may include the following: Pd/Cu, Pd/Fe, Pd/Ni, Pd/Zn, Pd/Ag, Pd/Cr, Pd/Sn, Pt/Cu, Pt/Fe, Pt/Ni, Pt/Zn, Pt/Ag, Pt/Cr, or Pt/Sn. Preferably the active metal combination may include Pd/Sn or Pt/Sn.

The preferred metal molar ratios of first metal to second metal may vary somewhat depending on the metals used in the catalyst. In some embodiments, the molar ratio of the first metal to the second metal preferably is from 10:1 to 1:10, e.g., from 4:1 to 1:4, from 2:1 to 1:2. In some cases, excess amount of the second metals can help distribute the first metal on the support. Selectivity to ethanol may be further improved by incorporating modified supports as described throughout the present specification.

Depending primarily on how the catalyst is manufactured, the active metals of the catalysts of the present invention may be dispersed throughout the modified support, coated on the outer surface of the support (egg shell) or decorated on the surface of the modified support.

Modified Supports

In addition to the active metals, the catalysts of the present invention further comprise a modified support that includes a support material, and support modifiers comprising i) a first support modifier comprising oxides of cobalt and ii) a second support modifier. Without being bound by theory, the second support modifier may adjust the acidity of the support material. For example, the acid sites, e.g. Brønsted or Lewis acid sites, on the support material may be adjusted by the second support modifier to favor selectivity to ethanol during the hydrogenation of acetic acid. The acidity of the support material may be adjusted by reducing the number or reducing the availability of Brønsted or Lewis acid sites on the support material. The support material may also be adjusted by changing the pKa of the support material by using the second support modifier. Unless the context indicates otherwise, the acidity of a surface or the number of acid sites thereupon may be determined by the technique described in F. Delannay, Ed., "Characterization of Heterogeneous Catalysts"; Chapter III:

Measurement of Acidity of Surfaces, p. 370-404; Marcel Dekker, Inc., N.Y. 1984, the entirety of which is incorporated herein by reference.

In addition to the metal precursors and preparation conditions employed, metal-support interactions may have a strong impact on selectivity to ethanol. In particular, the use of modified supports that adjust the acidity of the support to make the support less acidic or more basic can favor formation of ethanol over other hydrogenation products.

In one embodiment, the modified support is substantially free of tungsten, molybdenum, niobium, and tantalum.

As will be appreciated by those of ordinary skill in the art, support materials are selected such that the catalyst system is suitably active, selective and robust under the process conditions employed for the formation of ethanol. Suitable support materials may include, for example, stable metal oxide-based supports or ceramic-based supports. Preferred supports include supports, such as silica, silica/alumina, pyrogenic silica, high purity silica, or a carbon support (e.g., carbon black or activated carbon) and mixtures thereof. Other supports may be used in some embodiments of the present invention, including without limitation, iron oxide, alumina, titania, zirconia, magnesium oxide, carbon, graphite, high surface area graphitized carbon, activated carbons, and mixtures thereof.

In the case where silica is used as the silicaceous support, it is beneficial to ensure that the amount of aluminum, which is a common contaminant for silica, is low, preferably under 1 wt. %, e.g., under 0.5 wt. % or under 0.3 wt. %, based on the total weight of the modified support. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. In cases where the support comprises a support modifier in the range of from 2 wt. % to 10 wt. %, larger amounts of acidic impurities, such as aluminum, can be tolerated so long as they are substantially counter-balanced by an appropriate amount of a support modifier.

The surface area of the silicaceous support material, e.g., silica, preferably is at least about 50 $m^2/g$, e.g., at least about 100 $m^2/g$, at least about 150 $m^2/g$, at least about 200 $m^2/g$ or most preferably at least about 250 $m^2/g$. In one aspect, catalysts having a trilobe or quadrilobe shape may have an increased surface area. In terms of ranges, the silicaceous support material preferably has a surface area of from 50 to 600 $m^2/g$, e.g., from 100 to 500 $m^2/g$ or from 100 to 300 $m^2/g$. High surface area silica, as used throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The silicaceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 $cm^3/g$, e.g., from 0.7 to 1.5 $cm^3/g$ or from about 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes. In one aspect, the support material may have a shape having an increase surface area relative to the length, such as a trilobe or quadrilobe shape. Preferably, the silicaceous support material has a morphology that allows for a packing density of from 0.1 to 1.0 $g/cm^3$, e.g., from 0.2 to 0.9 $g/cm^3$ or from 0.5 to 0.8 $g/cm^3$. In terms of size, the silica support material preferably has an average particle size, e.g., meaning the diameter for spherical particles or equivalent spherical diameter for non-spherical particles, of from 0.01 to 1.0 cm, e.g., from 0.1 to 0.5 cm or from 0.2 to 0.4 cm. Since the two or more metal(s) that are disposed on or within the modified support are generally very small in size, they should not substantially impact the size of the overall catalyst particles. Thus, the above particle sizes generally apply to both the size of the modified supports as well as to the final catalyst particles.

In addition to the support material, the modified support also comprises support modifiers. In one embodiment, the catalyst comprises a first modifier selected from the group consisting of oxides of cobalt. The oxides of cobalt may include without limitation, $CoO_2$, $Co_2O_3$, and/or $CO_3O_4$. In one aspect, the oxides of cobalt may include a mixture of cobalt oxides and vanadium oxides, preferably is substantially equal amounts. In one embodiment, the modified support comprises from 0.2 to 7 wt. % cobalt, e.g., from 0.5 to 5 wt. % or from 1 to 4 wt. %. Vanadium oxide may be mixed with cobalt oxide to have a total loading of 0.2 to 7 wt. %. In one embodiment, the metal loading of cobalt is more than the metal loading of the first active metal.

Accordingly, without being bound by theory, modification and stabilization of support materials for the catalysts of the present invention by incorporation of non-volatile support modifiers having either the effect of: counteracting acid sites present upon the support surface or the effect of thermally stabilizing the surface makes it possible to achieve desirable improvements in selectivity to ethanol, prolonged catalyst life, or both. In general, support modifiers based on oxides in their most stable valence state will have low vapor pressures and thus have low volatility or are rather non-volatile. Accordingly, it is preferred that the support modifiers are provided in amounts sufficient to: (i) counteract acidic sites present on the surface of the support material; (ii) impart resistance to shape change under hydrogenation temperatures; or (iii) both. Without being bound by theory, imparting resistance to shape change refers to imparting resistance, for example, to sintering, grain growth, grain boundary migration, migration of defects and dislocations, plastic deformation and/or other temperature induced changes in microstructure.

In preferred embodiments, the second modifier comprises a basic support modifier having a low volatility or that is non-volatile. Low volatility modifiers have a rate of loss that is low enough such that the acidity of the support modifier is not reversed during the life of the catalyst. Such basic modifiers, for example, may be selected from the group consisting of alkaline earth metal oxides or metasilicates of the alkaline earth metals. In one aspect, the second support modifier is selected from the group consisting of oxides and metasilicates of any of magnesium, calcium, and mixtures thereof. The second support modifier is substantially free of other compounds such as alkali metals, Group IIB metals and Group IIIB metals. In one embodiment, the modified support comprises from 0.2 to 25 wt. % second support modifier, e.g., from 0.5 to 20 wt. % or from 3 to 9 wt. %.

As the second support modifier, e.g., calcium metasilicate, may tend to have a lower surface area than the support material, e.g., silicaceous support material, in one embodiment the support material comprises a silicaceous support material that includes at least about 80 wt. %, e.g., at least about 85 wt. % or at least about 90 wt. %, high surface area silica in order to counteract this effect of including a support modifier.

Although tin may be an active metal on the catalyst, in one embodiment the modified support is substantially free of tin. It is also preferred that the modified support is substantially free of ruthenium, rhenium, tungsten, molybdenum, niobium, and tantalum.

The total weight of the modified support, which includes the support material and the support modifiers, based on the total weight of the catalyst, preferably is from 75 wt. % to 99.9 wt. %, e.g., from 78 wt. % to 97 wt. %, or from 80 wt. % to 95 wt. %. The second support modifier preferably is provided in an amount sufficient to adjust the acidity, e.g., by reducing the number or reducing the availability of active Brønsted or Lewis acid sites, and more preferably to ensure that the surface of the support is substantially free of active Brønsted or Lewis acid sites. In preferred embodiments, the each of the support modifiers are present in an amount from 0.2 to 25 wt. %, e.g., from 0.5 to 20 wt. % or from 1.5 to 10 wt. %, based on the total weight of the catalyst. In one aspect, the support material is present in an amount from 50 wt. % to 99 wt. %, e.g., from 60 wt. % to 97 wt. % or from 70 wt. % to 95 wt. %.

In embodiments where substantially pure ethanol is to be produced at high selectivity, as indicated above, controlling the Brønsted acidity of the support material by incorporating a support modifier can be beneficial. One possible byproduct of the hydrogenation of acetic acid is ethyl acetate. According to the present invention, the support preferably includes a support modifier that is effective to suppress production of ethyl acetate, rendering the catalyst composition highly selective to ethanol. Thus, the catalyst composition preferably has a low selectivity toward conversion of acetic acid to ethyl acetate and highly undesirable by-products such as alkanes. The acidity of the support preferably is controlled such that less than 4%, e.g., less than 2% and most preferably less than 1%, of the acetic acid is converted to methane, ethane and carbon dioxide. The selectivity to diethyl acetate, diethyl ether and mixtures thereof of less than 1%, e.g., less than 0.5%. In addition, the acidity of the support may be controlled by using a pyrogenic silica or high purity silica as discussed above.

Catalysts of the present invention are particulate catalysts in the sense that, rather than being impregnated in a wash coat onto a monolithic carrier similar to automotive catalysts and diesel soot trap devices, the catalysts of the invention preferably are formed into particles, sometimes also referred to as beads or pellets, having any of a variety of shapes and the catalytic metals are provided to the reaction zone by placing a large number of these shaped catalysts in the reactor. Commonly encountered shapes include extrudates of arbitrary cross-section taking the form of a generalized cylinder in the sense that the generators defining the surface of the extrudate are parallel lines. As indicated above, any convenient particle shape including pellets, extrudates, spheres, spray dried microspheres, rings, pentarings, trilobes, quadrilobes and multi-lobal shapes may be used, although cylindrical pellets are preferred. Typically, the shapes are chosen empirically based upon perceived ability to contact the vapor phase with the catalytic agents effectively.

The catalyst composition of the present invention may be represented by the formula:

$$F_w S_x Co_y M_z SiO_v,$$

wherein: F is the first active metal selected from the group consisting of palladium, platinum, or combinations thereof; S is the second active metal selected from the group consisting of copper, iron, nickel, zinc, silver, chromium, tin, and combinations thereof; M is the metal of the second support modifier selected from the group consisting of magnesium, calcium, and mixtures thereof; w is from 0.00001 to 0.008, e.g., from 0.00002 to 0.0001; x is from 0.00005 to 0.002, e.g., from 0.00005 to 0.0001; y is from 0.025 to 0.5, e.g., from 0.03 to 0.4; z is from 0.01 to 0.2, e.g., from 0.02 to 0.09; and v being selected to satisfy valence requirements. In one embodiment, y is selected to be greater than w+x, and/or z is selected to be greater than w+x. Depending on the second support modifier, y may be at least 2z or more.

In one embodiment, the catalyst composition of the present invention may be represented by the formula:

$$Pt_w Sn_x Co_y Ca_z SiO_v,$$

wherein: w is from 0.00001 to 0.008, e.g., from 0.00002 to 0.0001; x is from 0.00005 to 0.002, e.g., from 0.00005 to 0.0001; y is from 0.025 to 0.5, e.g., from 0.03 to 0.4; z is from 0.01 to 0.2, e.g., from 0.02 to 0.09; and v being selected to satisfy valence requirements. In one embodiment, y is selected to be greater than w+x, and/or z is selected to be greater than w+x. In addition, y may be at least 2z or more.

In another aspect, the support material may comprise minor amounts of alumina. The second support modifier is chosen to balance the Brønsted acid sites present upon the surface of the support material created by alumina. In such aspects, the catalyst composition of the present invention may be represented by the formula:

$$F_w S_x Co_y M_z Al_u SiO_v,$$

wherein: F is the first active metal selected from the group consisting of palladium, platinum, or combinations thereof; S is the second active metal selected from the group consisting of copper, iron, nickel, zinc, silver, chromium, tin, and combinations thereof; M is the metal of the second support modifier selected from the group consisting of magnesium, calcium, and mixtures thereof; w is from 0.00001 to 0.008, e.g., from 0.00002 to 0.0001; x is from 0.00005 to 0.002, e.g., from 0.00005 to 0.0001; y is from 0.025 to 0.5, e.g., from 0.03 to 0.4; z is from 0.01 to 0.2, e.g., from 0.02 to 0.09; u is from 0.00001 to 0.01, e.g., from 0.00005 to 0.001; and v being selected to satisfy valence requirements. In aspect, z is greater than u.

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment, when the catalyst support comprises high purity silica, with calcium metasilicate as a support modifier, the catalyst activity may extend or stabilize, the productivity and selectivity of the catalyst for prolonged periods extending into over one week, over two weeks, and even months, of commercially viable operation in the presence of acetic acid vapor at temperatures of 125° C. to 350° C. at space velocities of greater than 2500 hr$^1$.

Processes for Making the Catalyst

The present invention also relates to processes for making the catalyst. Without being bound by theory, the process for making the catalyst may improve one or more of acetic acid conversion, ethanol selectivity and/or overall productivity. In one embodiment, the support material is modified with a cobalt support modifier and one or more additional support modifiers and the resulting modified support is subsequently impregnated with two or more active metals to form the catalyst composition. For example, the support material may be impregnated with a support modifier solution comprising a cobalt precursor and another support modifier precursor. The cobalt and other support modifier precursors can be present in the same or different solutions. These modifiers can also contact the support material at different times and/or in different order. After drying and calcination, the resulting modified support is impregnated with a second solution comprising two or more active metal precursors, followed by drying and calcination to form the final catalyst. In some cases either the cobalt or the other support modifier can be used impregnate the support material, followed by drying and calcination, before contacting the support material with the other support modifier and a second drying and calcination before introducing the active metal precursors.

In this embodiment, the support modifier solution may comprise a cobalt precursor and a support modifier metal precursor. The precursors preferably are comprised of salts of the respective metals in solution, which, when heated, are converted to elemental metallic form or to a metal oxide. Suitable cobalt precursors include acetate, nitrates, chlorides, for example. In some embodiments, cobalt may not interact with the support modifier metal precursor and is separately deposited on the support material, e.g., as discrete metal nanoparticles or as an amorphous metal mixture.

In some embodiments, the support modifiers may be added as particles to the support material. For example, along with cobalt, one or more support modifier precursors, if desired, may be added to the support material by mixing the support modifier particles with the support material, preferably in water. When mixed it is preferred for some support modifiers to use a powdered material of the support modifiers. If a powdered material is employed, the support modifier may be pelletized, crushed and sieved prior to being added to the support material.

As indicated, in most embodiments, the support modifier preferably is added through a wet impregnation step. Preferably, a support modifier precursor to the support modifier may be used. Some exemplary support modifier precursors include alkaline earth metal oxides, as well as preferably aqueous salts thereof. However, it is preferred that the support modifier precursor be free of rhenium, tungsten, molybdenum, niobium, and tantalum.

Impregnation of the two or more active metals onto the support material, e.g., modified support, may occur simultaneously (co-impregnation) or sequentially. In simultaneous impregnation, the two or more metal precursors are mixed together and added to the support material, preferably modified support, together followed by drying and calcination to form the final catalyst composition. With simultaneous impregnation, it may be desired to employ a dispersion agent, surfactant, or solubilizing agent, e.g., ammonium oxalate or an acid such as acetic or nitric acid, to facilitate the dispersing or solubilizing of the first, second and/or optional third metal precursors in the event the two precursors are incompatible with the desired solvent, e.g., water.

In sequential impregnation, the first metal precursor may be first added to the support material followed by drying and calcining, and the resulting material may then be impregnated with the second metal precursor followed by an additional drying step followed by a calcining step to form the final catalyst composition. Additional metal precursors (e.g., a third metal precursor) may be added either with the first and/or second metal precursor or in a separate third impregnation step, followed by drying and calcination. Of course, combinations of sequential and simultaneous impregnation may be employed if desired.

In embodiments where the two or more active metals, e.g., the first, second and third metals, are applied to the catalyst sequentially, i.e., in multiple impregnation steps, the catalyst may be said to comprise a plurality of "theoretical layers." For example, where tin is impregnated onto a support material followed by impregnation of an additional metal, the resulting catalyst may be said to have a first theoretical layer comprising tin and a second theoretical layer comprising the additional metal, e.g., Pt and/or Pd. As discussed above, in some aspects, more than one active metal precursor may be co-impregnated onto the support material in a single step such that a theoretical layer may comprise more than one metal or metal oxide. Preferably, the same metal precursor is not impregnated in multiple sequential impregnation steps leading to the formation of multiple theoretical layers containing the same metal or metal oxide. In this context, notwithstanding the use of the term "layers," it will be appreciated by those skilled in the art that multiple layers may or may not be formed on the support material depending, for example, on the conditions employed in catalyst formation, on the amount of metal used in each step and on the specific metals employed.

The use of a solvent, such as water, glacial acetic acid, a strong acid such as hydrochloric acid, nitric acid, or sulfuric acid, or an organic solvent, is preferred in the support modification step, e.g., for impregnating a support modifier precursor onto the support material. The support modifier solution comprises the solvent, preferably water, and at least one support modifier precursor. The solution is stirred and combined with the support material using, for example, incipient wetness techniques in which the support modifier precursor is added to a support material having the same pore volume as the volume of the solution Impregnation occurs by adding, optionally drop wise, a solution containing the precursors of the support modifiers to the dry support material. Capillary action then draws the support modifier into the pores of the support material. The thereby impregnated support can then be formed by drying, optionally under vacuum, to drive off solvents and any volatile components within the support mixture and depositing the support modifier on and/or within the support material. Drying may occur, for example, at a temperature from 50° C. to 300° C., e.g., from 100° C. to 200° C. or about 120° C., optionally for a period from 1 to 24 hours, e.g., from 3 to 15 hours or from 6 to 12 hours. The dried support may be calcined optionally with ramped heating, for example, at a temperature from 300° C. to 900° C., e.g., from 400° C. to 750° C., from 500° C. to 600° C. or at about 550° C., optionally for a period of time from 1 to 12 hours, e.g., from 2 to 10 hours, from 4 to 8 hours or about 6 hours, to form the final modified support. Upon heating and/or the application of vacuum, the metal(s) of the precursor(s) preferably decompose into their oxide or elemental form. In some cases, the completion of removal of the solvent may not take place until the catalyst is placed into use and/or calcined, e.g., subjected to the high temperatures encountered during operation. During the calcination step, or at least during the initial phase of use of the catalyst, such compounds are converted into a catalytically active form of the metal or a catalytically active oxide thereof.

Once formed, the modified supports may be shaped into particles having the desired size distribution, e.g., to form particles having an average particle size in the range from 0.2 to 0.4 cm. The supports may be extruded, pelletized, tabletized, pressed, crushed or sieved to the desired size distribution. Any of the known methods to shape the support materials into desired size distribution can be employed, and in preferred embodiments the shape may be a trilobe or quadrilobe. Alternatively, support pellets may be used as the starting material used to make the modified support and, ultimately, the final catalyst.

In one embodiment, the catalyst of the present invention may be prepared using a bulk catalyst technique. Bulk catalysts may be formed by precipitating precursors to support modifiers and the two or more active metals. The precipitating may be controlled by changing the temperature, pressure, and/or pH. In some embodiments, the bulk catalyst preparation may use a binder. A support material may not be used in a bulk catalyst process. Once precipitated, the bulk catalyst may be shaped by spraying drying, pelleting, granulating, tablet pressing, beading, or pilling. Suitable bulk catalyst techniques may be used such as those described in Krijn P. de Jong, ed., Synthesis of Solid Catalysts, Wiley, (2009), pg. 308, the entire contents and disclosure of which is incorporated by reference.

In one embodiment, the two or more active metals are impregnated onto the modified supports. A precursor of the active metals preferably is used in the metal impregnation step, such as a water soluble compound or water dispersible compound/complex that includes the active metals of interest. Similarly, precursors to one or more additional active metals may also be impregnated onto the modified support. Depending on the metal precursors employed, the use of a solvent, such as water, glacial acetic acid, nitric acid or an organic solvent, may be preferred to help solubilize one or more of the metal precursors.

In one embodiment, separate solutions of the metal precursors are formed, which are subsequently blended prior to being impregnated on the support material. For example, a first solution may be formed comprising a first metal precursor, and a second solution may be formed comprising the second metal precursor and optionally the third metal precursor. Either or both solutions preferably comprise a solvent, such as water, glacial acetic acid, hydrochloric acid, nitric acid or an organic solvent.

In one exemplary embodiment, a first solution comprising a first metal halide is prepared. The first metal halide optionally comprises a tin halide, e.g., a tin chloride such as tin (II) chloride and/or tin (IV) chloride. Optionally, a second metal precursor, as a solid or as a separate solution, is combined with the first solution to form a combined solution. The second metal precursor, if used, preferably comprises a second metal oxalate, acetate, halide or nitrate. The second metal precursor comprises an active metal, e.g., copper, iron, nickel, zinc, silver, chromium, or tin. A second solution is also prepared comprising a metal precursor to the first active metal, preferably a precious metal halide, such as a halide of platinum or palladium. The second solution is combined with the first solution or the combined solution, depending on whether the second metal precursor is desired, to form a mixed metal precursor solution. The resulting mixed metal precursor solution may then be added to the modified support, followed by drying and calcining to form the final catalyst composition as described above. The resulting catalyst may or may not be washed after the final calcination step. Due to the difficulty in solubilizing some precursors, it may be desired to reduce the pH of the first and/or second solutions, for example by employing an acid such as acetic acid, hydrochloric acid or nitric acid, e.g., 6 to 10 M $HNO_3$.

In another aspect, a second solution comprising a second metal oxalate is prepared, such as an oxalate of copper, iron, nickel, zinc, silver, chromium, or tin. In this embodiment, the second solution preferably further comprises an acid such as acetic acid, hydrochloric acid, phosphoric acid or nitric acid, e.g., 6 to 10 M $HNO_3$. A first solution is also formed comprising a metal oxalate, for example, an oxalate platinum or palladium, and further comprises an acid such as acetic acid, hydrochloric acid, phosphoric acid or nitric acid, e.g., 6 to 10 M $HNO_3$. The second solution is combined with the first solution or the combined solution, depending on whether the second metal precursor is desired, to form a mixed metal precursor solution. The resulting mixed metal precursor solution may then be added to the modified support, followed by drying and calcining to form the final catalyst composition as described above. The resulting catalyst may or may not be washed after the final calcination step.

In one embodiment, the impregnated modified support, is dried at a temperature from 100° C. to 140° C., from 110° C. to 130° C., or about 120° C., optionally from 1 to 12 hours, e.g., from 2 to 10 hours, from 4 to 8 hours or about 6 hours. If calcination is desired, it is preferred that the calcination temperature employed in this step is less than the calcination temperature employed in the formation of the modified support, discussed above. The second calcination step, for example, may be conducted at a temperature that is at least 50° C., at least 100° C., at least 150° C. or at least 200° C. less than the first calcination step, i.e., the calcination step used to form the modified support. For example, the impregnated catalyst may be calcined at a temperature from 200° C. to 500° C., from 300° C. to 400° C., or about 350° C., optionally for a period from 1 to 12 hours, e.g., from 2 to 10 hours, from 4 to 8 hours or about 6 hours.

In one embodiment, ammonium oxalate is used to facilitate solubilizing of at least one of the metal precursors, e.g., a tin precursor, as described in U.S. Pat. No. 8,211,821, the entirety of which is incorporated herein by reference. In this aspect, the first metal precursor optionally comprises an oxalate of palladium or platinum, and a second metal precursor optionally comprises an oxalate tin. Another active metal precursor, if desired, comprises a nitrate, halide, acetate or oxalate of chromium, copper, or tin. In this aspect, a solution of the second metal precursor may be made in the presence of ammonium oxalate as solubilizing agent, and the first metal precursor may be added thereto, optionally as a solid or a separate solution. If used, the third metal precursor may be combined with the solution comprising the first precursor and tin oxalate precursor, or may be combined with the second metal precursor, optionally as a solid or a separate solution, prior to addition of the first metal precursor. In other embodiments, an acid such as acetic acid, hydrochloric acid or nitric acid may be substituted for the ammonium oxalate to facilitate solubilizing of the tin oxalate. The resulting mixed metal precursor solution may then be added to the modified support, followed by drying and calcining to form the final catalyst composition as described above.

The specific precursors used in the various embodiments of the invention may vary widely. Suitable metal precursors may include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, sodium platinum chloride, and platinum ammonium nitrate, $Pt(NH_3)_4(NO_3)_2$. Generally, both from the point of view of economics and environmental aspects, aqueous solutions of soluble compounds of platinum and palladium are preferred. In one embodiment, the precious metal precursor is not a metal halide and is substantially free of metal halides, while in other embodiments, as described above, the precious metal precursor is a halide.

Use of Catalyst to Hydrogenate Carboxylic Acids

The process of hydrogenating a carboxylic acid, such as acetic acid to form ethanol according to one embodiment of the invention may be conducted in a variety of configurations using a fixed bed reactor or a fluidized bed reactor as one of skill in the art will readily appreciate. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions. The reaction temperature may the range from of 125° C. to 350° C., e.g., from 200° C. to 325° C., from 225° C. to about 300° C., or from 250° C. to about 300° C. The pressure may range from 100 kPa to 3000 kPa (about 1 to 30 atmospheres), e.g., from 100 kPa to 2700 kPa, or from 100 kPa to 2300 kPa. The reactants may be fed to the reactor at a gas hourly space velocities (GHSV) of greater than 500 $hr^{-1}$, e.g., greater than 1000 $hr^{-1}$, greater than 2500 $hr^{-1}$ and even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

In another aspect of the process of this invention, the hydrogenation is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 4:1, e.g., greater than 5:1 or greater than 10:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The acetic acid may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

In particular, using catalysts and processes of the present invention may achieve favorable conversion of acetic acid and favorable selectivity and productivity to ethanol. For purposes of the present invention, the term conversion refers to the amount of acetic acid in the feed that is convert to a compound other than acetic acid. Conversion is expressed as a mole percentage based on acetic acid in the feed.

The conversion of acetic acid (AcOH) is calculated from gas chromatography (GC) data using the following equation:

$$AcOH\ Conv.(\%) = 100 * \frac{mmol\ AcOH(feed\ stream) - mmol\ AcOH(GC)}{mmol\ AcOH(feed\ stream)}$$

For purposes of the present invention, the conversion may be at least 60%, e.g., at least 70% or at least 80%. Although catalysts that have high conversions are desirable, such as at least 80% or at least 90%, a low conversion may be acceptable at high selectivity for ethanol.

"Selectivity" is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Selectivity to ethanol (EtOH) is calculated from gas chromatography (GC) data using the following equation:

$$EtOH\ Sel.(\%) = 100 * \frac{mmol\ EtOH(GC)}{\frac{Total\ mmol\ C(GC)}{2} - mmol\ AcOH(feed\ stream)}$$

wherein "Total mmol C (GC)" refers to total mmols of carbon from all of the products analyzed by gas chromatograph.

For purposes of the present invention, the selectivity to ethanol of the catalyst is at least 80%, e.g., at least 85% or at least 88%. In embodiments of the present invention is also desirable to have low selectivity to undesirable products, such as methane, ethane, and carbon dioxide. The selectivity to these undesirable products is less than 4%, e.g., less than 2% or less than 1%. Preferably, no detectable amounts of these undesirable products are formed during hydrogenation. In several embodiments of the present invention, formation of alkanes is low, usually under 2%, often under 1%, and in many cases under 0.5% of the acetic acid passed over the catalyst is converted to alkanes, which have little value other than as fuel.

Productivity refers to the grams of a specified product, e.g., ethanol, formed during the hydrogenation based on the kilogram of catalyst used per hour. In one embodiment of the present invention, a productivity of at least 200 grams of ethanol per kilogram catalyst per hour, e.g., at least 400 grams of ethanol or least 600 grams of ethanol, is preferred. In terms of ranges, the productivity preferably is from 200 to 3,000 grams of ethanol per kilogram catalyst per hour, e.g., from 400 to 2,500 or from 600 to 2,000.

Some catalysts of the present invention may achieve a conversion of acetic acid of at least 10%, a selectivity to ethanol of at least 80%, and a productivity of at least 200 g of ethanol per kg of catalyst per hour. A subset of catalysts of the invention may achieve a conversion of acetic acid of at least 50%, a selectivity to ethanol of at least 80%, a selectivity to undesirable compounds of less than 4%, and a productivity of at least 600 g of ethanol per kg of catalyst per hour.

In another embodiment, the invention is to a crude ethanol product formed by processes of the present invention. The crude ethanol product produced by the hydrogenation process of the present invention, before any subsequent processing, such as purification and separation, typically will comprise primarily unreacted acetic acid and ethanol. In some exemplary embodiments, the crude ethanol product comprises ethanol in an amount from 15 wt. % to 70 wt. %, e.g., from 20 wt. % to 50 wt. %, or from 25 wt. % to 50 wt. %, based on the total weight of the crude ethanol product. Preferably, the crude ethanol product contains at least 22 wt. % ethanol, at least 28 wt. % ethanol or at least 44 wt. % ethanol. The crude ethanol product typically will further comprise unreacted acetic acid, depending on conversion, for example, in an amount from 0 to 80 wt %, e.g., from 5 to 80 wt %, from 20 to 70 wt. %, from 28 to 70 wt. % or from 44 to 65 wt. %. Since water is formed in the reaction process, water will also be present in the crude ethanol product, for example, in amounts ranging from 5 to 30 wt. %, e.g., from 10 to 30 wt. % or from 10 to 26 wt. %. Other components, such as, for example, esters, ethers, aldehydes, ketones, alkanes, and carbon dioxide, if detectable, collectively may be present in amounts less than 10 wt. %, e.g., less than 6 or less than 4 wt. %. In terms of ranges other components may be present in an amount from 0.1 to 10 wt. %, e.g., from 0.1 to 6 wt. %, or from 0.1 to 4 wt. %. Thus, exemplary crude ethanol compositional ranges in various embodiments of the invention are provided below in Table 2.

TABLE 2

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 15-70 | 15-70 | 20-50 | 25-50 |
| Acetic Acid | 5-80 | 20-70 | 28-70 | 44-65 |
| Water | 5-30 | 5-30 | 10-30 | 10-26 |
| Other | <10 | <10 | <6 | <4 |

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377 to Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. See also, U.S. Pat. No. 5,821,111 to Grady et al., which discloses a process for converting waste biomass through gasification into synthesis gas as well as U.S. Pat. No. 6,685,754 to Kindig et al., the disclosures of which are incorporated herein by reference.

Alternatively, acetic acid in vapor form may be taken directly as crude product from the flash vessel of a methanol carbonylation unit of the class described in U.S. Pat. No. 6,657,078 to Scates et al., the entirety of which is incorporated herein by reference. The crude vapor product, for example, may be fed directly to the ethanol synthesis reaction zones of the present invention without the need for condensing the acetic acid and light ends or removing water, saving overall processing costs.

Ethanol, obtained from hydrogenation processes of the present invention, may be used in its own right as a fuel or subsequently converted to ethylene which is an important commodity feedstock as it can be converted to polyethylene, vinyl acetate and/or ethyl acetate or any of a wide variety of other chemical products. In another application, the finished ethanol composition may be dehydrated to produce ethylene. Any known dehydration catalyst, such as zeolite catalysts or phosphotungstic acid catalysts, can be employed to dehydrate ethanol, as described in copending U.S. Pub. Nos. 2010/0030002 and 2010/0030001 and WO2010146332, the entire contents and disclosures of which are hereby incorporated by reference.

Ethanol may also be used as a fuel, in pharmaceutical products, cleansers, sanitizers, hydrogenation transport or consumption. Ethanol may also be used as a source material for making ethyl acetate, aldehydes, and higher alcohols, especially butanol. In addition, any ester, such as ethyl acetate, formed during the process of making ethanol according to the present invention may be further reacted with an acid catalyst to form additional ethanol as well as acetic acid, which may be recycled to the hydrogenation process.

The invention is described in detail below with reference to numerous embodiments for purposes of exemplification and illustration only. Modifications to particular embodiments within the spirit and scope of the present invention, set forth in the appended claims, will be readily apparent to those of skill in the art.

The following examples describe the procedures used for the preparation of various catalysts employed in the process of this invention.

EXAMPLES

Catalyst Preparation

Example 1

(A) [$SiO_2$—$CaSiO_3$(5.6)—$Co_3O_4$(6.7)] (Modified Support); Scale: ~100 g

First, an aqueous solution of cobalt(II) acetate tetrahydrate was prepared by dissolving 21.132 g (0.0848 mol) in 60 mL of deionized $H_2O$. The resulting deep-red, homogeneous solution was then diluted to a total volume of 108 mL with deionized $H_2O$. Separately, 95 g of the catalyst support (4.5 mm Trilobes impregnated with $CaSiO_3$) was placed in a 1 L round-bottomed flask. The metal solution was then added to the catalyst support using incipient wetness technique. Next, the round-bottomed flask containing the impregnated support was attached to a rotor evaporator, and the solid was dried to constant weight under vacuum (slow rotation, bath temperature 80° C.). The solid was then transferred into a large porcelain dish and dried overnight at 120° C. under circulating air. The dried solid was then calcined at 550° C. under air for six hours using a heating rate of 3 degree/min. The resulting modified support was stored in a dry environment and subsequently used without further treatment for the preparation of the final catalyst.

(B) [$SiO_2$—$CaSiO_3$(5.6)—$Co_3O_4$(6.7)]—Pt(0.5)—Sn(0.6) (Finished Catalyst); Scale: ~50 g Platinum and tin are both added simultaneously (1-step impregnation) as aqueous solution. The following preparation uses 50 g of the modified, [$SiO_2$—$CaSiO_3$(5.6)—$Co_3O_4$(6.7)] catalyst support. First, 0.9086 g (6.39 mmol) of solid ammonium oxalate monohydrate was added to 28 mL of deionized $H_2O$ and dissolved with stirring at room temperature. Next, 0.5286 g (2.56 mmol) of tin(II) oxalate was added to the solution. The mixture was stirred for another ten minutes at room temperature resulting in a clear, colorless solution. Separately, 3.4624 g of the platinum(II) oxalate solution (7.28 wt. % Pt) was diluted to a total volume of 26 mL using deionized $H_2O$. The dark blue Pt solution was then added to the tin(II) solution with stirring resulting in a yellow-brown, homogeneous solution. The solution was aged with stirring for 15 min at room temperature and then used as prepared for the impregnation of the catalyst support. After adding the metal solution to the catalyst support (incipient wetness technique), the material was left standing for one hour at room temperature, and then evacuated to dryness (rotor evaporator). The solid was then transferred into a large porcelain dish and dried overnight at 120° C. under circulating air. The dried material was then calcined (350° C. for 6 hours), using the following temperature program: 2 h/160° C., ramp 3 degree/min; 6 h/350° C., ramp 3 degree/min). After calcination, the material should be stored in a dry environment and protected from moisture.

Example 2 used a similar catalyst preparation procedure as Example 1, but used 3 mm catalyst support pellets instead of the trilobes. Example 3 also used a similar catalyst preparation procedure, but utilized vanadium as a support modifier in addition to cobalt and calcium. The catalysts of Comparative Examples 1 and 2 was prepared similarly to Example 1, but without the cobalt support modifier. Comparative Example 1 used a 3 mm pellet catalyst support while Comparative Example 2 utilized a 4 mm trilobe catalyst support. Comparative Examples 3 and 4 used a similar catalyst procedure as Example 1, except that no support modifier was used.

Catalyst Testing

The catalysts were tested for performance data for acetic acid hydrogenation to ethanol and ethyl acetate. The testing procedure involved 10 mL of solid catalyst (for example, 3 mm pellets, 1:1 v/v diluted with 3 mm glass beads) at a reaction temperature of 260° C. and a pressure of 2169.75 kPa (300 psig). The flow rate of $H_2$ was 342 sccm and the HOAc flow rate was 0.092 g/min. Thus, [$H_2$]/[HOAc]=9.5 at a GHSV of 2,268 $h^{-1}$. Conversions and selectivities were measured. The results from the catalyst testing are summarized in Table 3.

TABLE 3

Summary of catalyst performance data for the acetic acid hydrogenation to ethanol and ethyl acetate.

| Example No. | Catalyst | Catalyst Shape | HOAc Conv. (%) | Selectivity (%) EtOH | EtOAc | AcH |
|---|---|---|---|---|---|---|
| 1 | [$SiO_2$—$CaSiO_3$(5.6)—$Co_3O_4$(6.7)]—Pt(0.5)—Sn(0.6) | 3 mm pellet | 70 | 89 | 8 | 1 |
| 2 | [$SiO_2$—$CaSiO_3$(5.6)—$Co3O_4$(6.7)]—Pt[0.5]—Sn(0.6) | 4 mm trilobe | 87 | 91 | 7 | 1 |
| 3 | [$SiO_2$—$CaSiO_3$(6)—$Co_3O_4$—$V_2O_5$]—Pt(0.5)—Sn(0.6) | 3 mm pellet | 70 | 88 | 10 | 1 |
| Comp. 1 | [$SiO_2$—$CaSiO_3$(6.0)]—Pt(1.09)—Sn(1.23) | 3 mm pellet | 67 | 85 | 11 | 2 |
| Comp. 2 | [$SiO_2$—$CaSiO_3$(6.0)]—Pt(1.09)—Sn(1.23) | 4 mm trilobe | 48 | 88 | 11 | 1 |
| Comp. 3 | [$SiO_2$]—Pt(1.7)—Sn(4.4) | 3 mm pellet | 85 | 69 | 29 | 2 |
| Comp. 4 | [$SiO_2$]—Pt(1.7)—Sn(0.82) | 3 mm pellet | 73 | 89 | 9 | 2 |

As can be seen from the table, the combination of conversion of acetic acid and selectivity to ethanol was at its highest for the Examples prepared in accordance with the present invention. That is, the Examples prepared in accordance with the present invention were found to have superior or equivalent performance to the comparative examples, but with less active metal loading. In addition, while the catalyst trilobe shape was found to have a detrimental effect in terms of conversion for catalysts without cobalt in Comparative Examples 1 and 2, while the trilobe structure improved conversion for catalysts utilizing cobalt as a support modifier in Example 2.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A catalyst for hydrogenating acetic acid and esters thereof, comprising:
   a) active metals comprising:
      1) a first metal selected from the group consisting of palladium, platinum, and combinations thereof, and
      2) a second metal selected from the group consisting of copper, iron, nickel, zinc, silver, chromium, tin, and combinations thereof; and
   b) a modified support, wherein the active metals are disposed on the modified supports, wherein the modified support further comprises:
      1) a support material selected from the group consisting of silica, silica/alumina, pyrogenic silica, high purity silica, carbon, and mixtures thereof, and
      2) support modifiers comprising:
         i) from 0.2 wt. % to 10 wt. % of a first modifier selected from the group consisting of oxides of cobalt, and
         ii) from 0.2 wt. % to 25 wt. % of a second modifier selected from the group consisting of alkaline earth metal oxides and metasilicates of the alkaline earth metals,
   wherein the first metal is present in an amount of less than 1 wt. % and the total content of the first and second metals is in an amount from 0.1 wt. % to 10 wt. %, based on the total weight of the catalyst.

2. The catalyst of claim 1, wherein the support material has a morphology selected from the group consisting of pellets, extrudates, spheres, spray dried microspheres, rings, pentarings, trilobes, quadrilobes, multi-lobal shapes, or flakes.

3. The catalyst of claim 2, wherein the support material has a morphology of trilobes of 4 mm in length.

4. The catalyst of claim 1, wherein the total amount of the first and second active metals is less than the amount of the first modifier.

5. The catalyst of claim 1, wherein the second metal comprises tin.

6. The catalyst of claim 1, wherein the second modifier comprises calcium metasilicate.

7. The catalyst of claim 1, wherein the first metal is present in an amount from 0.3 to 0.7 wt. %.

8. The process for producing ethanol, comprising contacting a feed stream comprising acetic acid, ethyl acetate, or mixtures thereof and hydrogen in a reactor in the presence of a catalyst of claim 1, wherein the hydrogenation is performed in a vapor phase at a temperature of from 125° C. to 350° C., an absolute pressure of 10 kPa to 3000 kPa, and a hydrogen to acetic acid mole ratio of greater than 4:1.

9. The process of claim 8, wherein the catalyst is capable of a selectivity to ethanol of at least 80%.

10. The process of claim 8, wherein the catalyst has a productivity that decreases less than 6% per 100 hours of catalyst usage.

11. The process of claim 8, wherein the catalyst is capable of an acetic acid conversion that is greater than 70%.

12. The process of claim 8, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

13. The process of claim 8, further comprising dehydrating the ethanol obtained during the hydrogenation to produce ethylene.

14. A catalyst for hydrogenating acetic acid and esters thereof, comprising:
   a) active metals comprising:
      1) a first metal selected from the group consisting of palladium, platinum, and combinations thereof, and
      2) a second metal selected from the group consisting of copper, iron, nickel, zinc, silver, chromium, tin, and combinations thereof and
   b) a modified support, wherein the active metals are disposed on the modified supports, wherein the modified support further comprises:
      1) a support material selected from the group consisting of silica, silica/alumina, pyrogenic silica, high purity silica, carbon, and mixtures thereof, and
      2) support modifiers comprising:
         i) from 0.2 wt. % to 10 wt. % of a first modifier selected from the group consisting of oxides of cobalt, and
         ii) from 0.2 wt. % to 25 wt. % of a second modifier selected from the group consisting of alkaline earth metal oxides and metasilicates of the alkaline earth metals,
   wherein the silicaceous support has a morphology selected from the group consisting of pellets, extrudates, spheres, spray dried microspheres, rings, pentarings, trilobes, quadrilobes, multi-lobal shapes, or flakes.

15. The catalyst of claim 14, wherein first metal is present in an amount of less than 1 wt. % and the total content of first metal and second metal is in an amount from 0.1 wt. % to 10 wt. %, based on the total weight of the catalyst.

16. The catalyst of claim 14, wherein the alkaline earth metal oxide or metasilicate of an alkaline earth metal is present in an amount from 0.2 wt. % to 25 wt. %.

17. The catalyst of claim 14, wherein the oxide or metasilicate of an alkaline earth metal comprises calcium metasilicate.

18. The catalyst of claim 14, further comprising vanadium oxide.

* * * * *